US008444932B2

(12) United States Patent (10) Patent No.: US 8,444,932 B2
Spanuth et al. (45) Date of Patent: May 21, 2013

(54) D-DIMER, TROPONIN, AND NT-PROBNP FOR PULMONARY EMBOLISM

(75) Inventors: Eberhard Spanuth, Dossenheim (DE); Boris Ivandic, Munich (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/020,346

(22) Filed: Feb. 3, 2011

(65) Prior Publication Data

US 2011/0129936 A1 Jun. 2, 2011

Related U.S. Application Data

(63) Continuation of application No. PCT/EP2009/005849, filed on Aug. 12, 2009.

(30) Foreign Application Priority Data

Aug. 13, 2008 (EP) .................................. 08162303

(51) Int. Cl.
*G01N 33/68* (2006.01)
*G01N 33/48* (2006.01)

(52) U.S. Cl.
USPC ............... 422/430; 436/63; 436/86; 436/501; 422/68.1

(58) Field of Classification Search
USPC ............. 436/63, 86, 161, 173, 501; 422/68.1, 422/430; 435/13
See application file for complete search history.

(56) References Cited

U.S. PATENT DOCUMENTS

| 5,744,305 | A | 4/1998 | Fodor et al. |
| 6,780,606 | B1 | 8/2004 | Jackowski |
| 2003/0119064 | A1 | 6/2003 | Valkirs et al. |
| 2003/0199000 | A1 | 10/2003 | Valkirs et al. |
| 2004/0121343 | A1* | 6/2004 | Buechler et al. ................... 435/6 |
| 2004/0126767 | A1* | 7/2004 | Anderberg et al. ............... 435/6 |
| 2004/0203083 | A1 | 10/2004 | Beuchler et al. |
| 2004/0219509 | A1 | 11/2004 | Valkirs et al. |
| 2004/0253637 | A1 | 12/2004 | Buechler et al. |
| 2005/0255484 | A1 | 11/2005 | Valkirs et al. |
| 2007/0224643 | A1* | 9/2007 | McPherson et al. ........... 435/7.1 |
| 2007/0269836 | A1* | 11/2007 | McPherson et al. ........... 435/7.4 |
| 2008/0070234 | A1 | 3/2008 | Spinke et al. |
| 2010/0055683 | A1* | 3/2010 | Snider et al. ..................... 435/6 |

FOREIGN PATENT DOCUMENTS

| EP | 0648228 | B1 | 11/1998 |
| WO | 00/67633 | A2 | 11/2000 |
| WO | 02/083913 | A1 | 10/2002 |
| WO | 02/089657 | A3 | 11/2002 |
| WO | 2008/017928 | A3 | 2/2008 |

OTHER PUBLICATIONS

International Search Report issued Dec. 22, 2009 in PCT Application No. PCT/EP2009/005849.

International Preliminary Report on Patentability issued Oct. 1, 2010 in PCT Application No. PCT/EP2009/005849.
Anderson, Page A. W. et al., "Molecular Basis of Human Cardiac Troponin T Isoforms Expressed in the Developing, Adult, and Failing Heart," Circulation Research, 1995, pp. 681-686, vol. 76 No. 4.
Bonow, Robert O., "New Insights Into the Cardiac Natriuretic Peptides," Circulation, 1996, pp. 1946-1950, vol. 93.
Brill-Edwards, Patrick and Lee, Agnes, "D-Dimer Testing in the Diagnosis of Acute Venous Thromboembolism," Thrombosis and Haemostasis, 1999, pp. 688-694, vol. 82, No. 2.
Delabays, Alain, "The role of biomarkers in the evaluation of the patient with dyspnea, chest pain or syncope," Revue Médicale Suisse, Nov. 14, 2007, pp. 2605-2608, vol. 3, No. 133, Abstract in English.
Ferrieres, Gaelle et al., "Human cardiac troponin I: precise identification of antigenic epitopes and prediction of secondary structure," Clinical Chemistry, 1998, pp. 487-493, vol. 44, No. 3.
Gaffney, P. J. and Brasher, M., "Subunit Structure of the Plasmin-Induced Degradation Products of Crosslinked Fibrin," Biochimica et Biophysica Acta, 1973, pp. 308-313, vol. 295.
Ghanima, W. et al., "D-dimer level is associated with the extent of pulmonary embolism," Thrombosis Research, Jan. 1, 2007, pp. 281-288, vol. 120, No. 2.
Goldhaber, Samuel Z., "Pulmonary embolism," The Lancet, Apr. 17, 2004, pp. 1295-1305, vol. 363, No. 9417.
Harrison, Alex and Amundson, Stanley, "Evaluation and management of the acutely dyspneic patient: the role of biomarkers," American Journal of Emergency Medicine, May 1, 2005, pp. 371-378, vol. 23, No. 3.
Karl, J. et al., "Development of a novel, N-Terminal-proBNP (NT-proBNP) assay with a low detection limit," Scandinavian Journal of Clinical and Laboratory Investigation, 1999, pp. 177-181, vol. 59, Supplement 230.
Knecht, M. F. et al., "Evaluation of Plasma D-Dimer in the Diagnosis and in the Course of Fibrinolytic Therapy of Deep Vein Thrombosis and Pulmonary Embolism," Thrombosis Research, 1992, pp. 213-220, vol. 67, No. 2.
Kulstad, Erik B. et al., "A Rapid Quantitative Turbimetric D-dimer Assay Has High Sensitivity for Detection of Pulmonary Embolism in the ED," American Journal of Emergency Medicine, 2004, pp. 111-114, vol. 22.
Lainchbury, John G. et al., "Brain Natriuretic Peptide and N-Terminal Brain Natriuretic Peptide in the Diagnosis of Heart Failure in Patients With Acute Shortness of Breath," Journal of the American College of Cardiology, 2003, pp. 728-735, vol. 42, No. 4.
Lippi, Giuseppe and Guidi, Gian Cesare, "Effect of Specimen Collection on Routine Coagulation Assays and D-Dimer Measurement," Clinical Chemistry, 2004, pp. 2150-2152, vol. 50.

(Continued)

*Primary Examiner* — Maureen Wallenhorst

(74) *Attorney, Agent, or Firm* — Roche Diagnostics Operations, Inc.

(57) ABSTRACT

The present invention relates to a method of diagnosing acute pulmonary embolism (PE) in a subject including a) determining the amount of fibrin-fibrinogen degradation products, in particular D-dimer in a sample of the subject; b) determining the amount of a natriuretic peptide in a sample of the subject; c) determining the amount of a cardiac troponin in a sample of the subject; and d) comparing the amounts determined in steps a) to c) to reference amounts, thereby establishing the diagnosis. Included is also a method of deciding on a therapy of a subject diagnosed with PE and a method of monitoring the therapy.

20 Claims, No Drawings

OTHER PUBLICATIONS

Melanson, Stacy E. F. et al., "Combination of D-Dimer and Amino-Terminal Pro-B-Type Natriuretic Peptide Testing for the Evaluation of Cyspneic Patients With and Without Acute Pulmonary Embolism," Archives of Pathology & Laboratory Medicine, Sep. 2006, pp. 1326-1329, vol. 130, No. 9.

Mueller, Thomas et al., "Long-term stability of endogenous B-type natriuretic peptide (BNP) and amino terminal proBNP (NT-proBNP) in frozen plasma samples," Clinical Chemistry and Laboratory Medicine, 2004, pp. 942-944, vol. 42, No. 8.

Nolan, John P. and Sklar, Larry A., "Suspension array technology: evolution of the flat-array paradigm," Trends in Biotechnology, Jan. 2002, pp. 9-12, vol. 20, No. 1.

"Interdisciplinary S2 guideline Diagnosis and treatment of leg and pelvic venous thrombosis and of pulmonary embolism," Phlebologie, Dec. 20, 2004, pp. 47-64, vol. 34, Schattauer GmbH, with partial translation of p. 47 and pp. 55-64.

Potter, Lincoln R. et al., "Natriuretic Peptides: Their Structures, Receptors, Physiologic Functions and Therapeutic Applications," H.H.H.W. Schmidt et al. Editors, cGMP: Generators, Effectors and Therapeutic Implications, Handbook of Experimental Pharmacology, 2009, pp. 341-366, vol. 191, Springer-Verlag Berlin Heidelberg.

Sanz, M. P. et al., "Comparison of BNP and NT-proBNP Assays in the Approach to the Emergency Diagnosis of Acute Dyspnea," Journal of Clinical Laboratory Analysis, 2006, pp. 227-232, vol. 20, No. 6.

Smith, M. W. et al., "Delayed metabolism of human brain natriuretic peptide reflects resistance to neutral endopeptidase," Journal of Endocrinology, 2000, pp. 239-246, vol. 167.

Stein, Paul D. et al., "D-Dimer for the Exclusion of Acute Venous Thrombosis and Pulmonary Embolism A Systematic Review," Annals of Internal Medicine, 2004, pp. 589-602, vol. 140.

Stötzer, K.-E. et al., "Assays of Fibrin Degradation Products and Their Clinical Relevance," Haemostasis, 1988, pp. 174, vol. 18, Supplement 2.

Van Beck, Edwin J. R. and Ten Cate, Jan W., "The Diagnosis of Venous Thromboembolism: An Overview," Venous Thromboembolism: An Evidence-Based Atlas edited by Russel Hull et al., 1996, Chapter 12, pp. 93-99, Futura Publishing Co., Armonk, New York.

Wolfe, Mark W. et al., "Prognostic significance of right ventricular hypokinesis and perfusion lung scan defects in pulmonary embolism," American Heart Journal, pp. 1371-1375, vol. 127, No. 5, 1994.

Wu, Alan H. B. et al., "Analytical and Clinical Evaluation of the Bayer ADVIA Centaur Automated B-Type Natriuretic Peptide Assay in Patients with Heart Failure: A Multisite Study," Clinical Chemistry, 2004, pp. 867-873, vol. 50, No. 5.

Yeo, Kiang-Teck J. et al., Multicenter evaluation of the Roche NT-proBNP assay and comparison to the Biosite Triage BNP assay, Clinica Chimica Acta, 2003, pp. 107-115, vol. 338.

* cited by examiner

D-DIMER, TROPONIN, AND NT-PROBNP FOR PULMONARY EMBOLISM

RELATED APPLICATIONS

This application is a continuation of PCT/EP2009/005849 filed Aug. 12, 2009 and claims priority to EP 08162303.5 filed Aug. 13, 2008.

FIELD OF THE INVENTION

The present invention relates to a diagnostic method and, in particular, to a method of diagnosing acute pulmonary embolism (PE) in a subject, comprising determining the amounts of fibrin-fibrinogen derived degradation products, in particular D-dimer, a natriuretic peptide, in particular NT-proBNP, and a cardiac Troponin in a sample of the subject and comparing the said amounts to reference amounts. Further, the present invention also relates to a method of differentiating between various degrees of acute PE in a subject, comprising determining the amounts of fibrin-fibrinogen derived degradation products, in particular D-dimer, a natriuretic peptide, in particular NT-proBNP, and a cardiac Troponin in a sample of the subject and comparing the said amounts to reference amounts. The present invention also encompasses devices and kits for carrying out the aforementioned methods.

BACKGROUND OF THE INVENTION

PE may be a life threatening medical event requiring hospitalization. The characteristic clinical symptoms of acute PE include acute shortness of breath, collapse-like conditions and chest pain. PE is caused by thrombosis which often occurs in femoral veins. Moreover, the thrombosis may be accompanied by further conditions such as genetically caused defects in the blood coagulation cascade or cancer.

As a consequence of thrombosis, a floating thrombus may enter and occlude the pulmonary artery. The size of the embolus determines the position of the arterial occlusion. The occlusion of a pulmonary artery results in a increased ventricular pressures and volume overload of the right heart and, as a consequence thereof, will often lead to a poor function of the left heart and circulatory failure.

PE may occur as a singular event accompanied by the aforementioned acute clinical symptoms which result, in particular in the case of emergency patients, in hospitalization or may be the result of multiple smaller PE whereby only the most recent one is accompanied with the said clinical symptoms. The latter condition is called "multiple PE" hereinafter.

Pulmonary embolism (PE) is a widespread, severe and often lethal health problem. The annual incidence for deep vein thrombosis (DVT) and PE in the general population of the Western industrialized countries may be estimated at 0.5 to 1.0 per 1000 respectively (van Beek E J R, ten Cate J W. The diagnosis of venous thromboembolism: an overview. In: Hull R D, Raskob G E, pineo G F, eds. Venous Thromboembolism: an evidence-based atlas. Armonkl: Futura Publishing Co, 1996: 93-9). There is, however, a high number of unrecognized and untreated cases, as is shown by autopsy studies. Diagnosis is difficult and hard to carry out, because PE has a wide range of clinical presentations. The most common clinical symptoms of acute PE are dyspnea, chest pain and syncope. These symptoms are similar to those of acute coronary syndrome. Approximately 30% of patients in an internal emergency unit show chest pain and respiratory symptoms, which, at first sight, point towards acute coronary syndrome. However, more than 50% of these patients do not suffer from acute coronary syndrome. The symptoms that these patients show, are related to extra-cardial causes, which are dominated by PE and other pulmonary diseases. In patients with reasonable clinical evidence for PE, first line diagnostic tests, such as ECG, chest X-ray and blood-gas analysis are indicated to assess the clinical probability of PE and the general condition of the patient. A diagnostic exclusion of PE can be made by determining the concentrations of D-dimer (a low level suggests exclusion of PE). However, elevated D-dimer levels are unspecific and are found in conditions associated with intravascular disseminated activation processes of haemostasis, like inflammatory reactions, e.g. infections or sepsis or malignous tumors. Confirmation diagnosis of PE is established by chest x-ray, lung scintigraphy, pulmonary angiography, contrast enhanced, spiral computerized tomography, and echocardiography.

It is important to initiate therapy as soon as possible. Early fatality is high and depends on the severity of the disease as well as on the existence of accompanying diseases (in particular cardiovascular diseases). Approximately 90% of the deaths occur within two hours after onset of the symptoms. The mortality of untreated PE during the hospital stay is 30%, and can be lowered to approximately 2 to 8% by applying appropriate therapies.

The treatment success substantially depends on the initiation of early therapeutic measures depending on the severity of the disease. Accordingly, in every case of a clinical suspicion of PE, this suspicion should be clarified by diagnostic and prognostic measures. The basis for this, on the other hand, is the existence of appropriate diagnostic testing parameters and testing methods, allowing the diagnostic as well as the prognostic estimation while being appropriate for emergency situations.

Due to the uncertainty about their diagnostic/prognostic value, the cardiac biomarkers troponin and natriuretic peptides were not included into therapy guidelines (anticoagulation, thrombolysis, embolectomy).

The decision about the appropriate therapy for the individual patient requires, besides the diagnosis, also risk stratification and prognosis estimation in a clinical emergency situation. When the diagnosis is certain, the essential therapeutic question is, whether anticoagulation with heparins will be sufficient, or whether additional measures, like thrombolysis or embolectomy, are necessary. Thrombolysis and embolectomy should only be used in cases of massive PE, due to the risks of complications and side effects, even when no contraindications exist.

In accordance with the actual guidelines, the hemodynamic situation of the patient is crucial for the classification into risk groups I-IV (hemodynamically stable to reanimation). While D-dimer is already established for the primary diagnosis to exclude PE, a further classification by using further markers is not possible, for the time being.

Thus, the technical problem underlying the present invention may be seen as the provision of means and methods for complying with the aforementioned needs. The technical problem is solved by the embodiments characterized in the claims and herein below.

SUMMARY OF THE INVENTION

Accordingly, the present invention relates to a method of diagnosing acute PE in a subject suspected to suffer from acute PE comprising a) determining the amount of a marker of intravascular activation of coagulation and fibrinolysis from the group of fibrin-fibrinogen degradation products, preferably of D-dimer, in a sample of the subject.

b) determining the amount of a natriuretic peptide, preferably NT-proBNP in a sample of the subject;

c) determining the amount of a cardiac troponin, preferably troponin T or troponin I, in particular troponin T, in a sample of the subject;

d) comparing the amounts determined in steps a) to c) to reference amounts, thereby establishing the said diagnosis.

DETAILED DESCRIPTION OF THE INVENTION

Diagnosing as used herein refers to assessing the probability according to which a subject suffers from the diseases referred to in this specification. As will be understood by those skilled in the art, such an assessment is usually not intended to be correct for 100% of the subjects to be diagnosed. The term, however, requires that a statistically significant portion of subjects can be diagnosed to suffer from the said disease (e.g. a cohort in a cohort or case-control study). Whether or not a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

Diagnosing according to the present invention also includes monitoring, confirmation, subclassification and prediction of the relevant disease, symptoms or risks thereof. Monitoring relates to keeping track of an already diagnosed disease, or complication, e.g. to analyze the progression of the disease or the influence of a particular treatment on the progression of disease or complication. Confirmation relates to the strengthening or substantiating a diagnosis already performed using other indicators or markers. Subclassification relates to further defining a diagnosis according to different subclasses of the diagnosed disease, e.g. defining according to mild and severe forms of the disease. Prediction relates to prognosing a disease or complication before other symptoms or markers have become evident or have become significantly altered.

The term "pulmonary embolism ("PE") as used herein refers to a disease or condition accompanied with the aforementioned clinical symptoms of PE, i.e. acute shortness of breath, collapse-like conditions and/or chest pain and, optionally, right ventricular volume overload of the heart which may be accompanied by a poor support of the left heart.

The term "subject" as used herein relates to animals, preferably mammals, and, more preferably, humans. However, it is envisaged by the present invention that the subject shall, preferably, exhibit the aforementioned apparent clinical symptoms of a PE.

The method of the present invention comprises the determination of at least three markers, whereby in step a) at least one marker of intravascular activation of coagulation and fibrinolysis, in step b) at least one marker of cardiac ischemia and necrosis, and in step c) at least one neurohumoral marker of ventricular volume and pressure overload is determined.

Cardiac troponin I and T are released depending on the degree of right ventricular ischemia, right ventricular damage, and myocyte necrosis caused by right ventricular pressure overload and hypoxia due to the increased pulmonary arterial pressure in PE. Elevated serum concentrations of cardiac troponin I and T were found in 11 to 50% of patients with PE. Accordingly, determination of troponin as such only gives limited information, as the majority of patients with PE (>50%) do not have an elevated troponin level. In addition, the troponin levels are only moderately raised in PE patients, compared to acute coronary syndrome ("ACS"), and the elevation is short-term. A further limitation, however, lies in the fact that troponin release starts only 6 to 12 hours after the occurrence of PE.

Natriuretic peptides are released as a consequence of ventricular wall stress and volume overload. They are, therefore, established as diagnostic and prognostic markers in patients with ventricular dysfunction (heart failure). The prohormone proBNP is synthesized in ventricular myocytes, therefore, an elevation in serum, as a consequence of elevated synthesis rate after the occurrence of myocardial wall stress and volume overload, occurs only some hours later. Elevated serum or plasma concentrations of the natriuretic peptides BNP and NT-proBNP are associated with right ventricular volume overload and dysfunction caused by increased pulmonary arterial pressure in PE. A further limitation, accordingly, is the fact that natriuretic peptides are also elevated in other extracardial diseases associated with right ventricular volume overload, e.g. chronic pulmonary diseases like COPD or primary pulmonary hypertension. Accordingly, natriuretic peptides, like troponins, only permit a limited prognosis and PE when interpreted alone, due to a lack of specificity.

Using cardiac troponins or natriuretic peptides alone for risk stratification of patients with PE, only a patient group with low risk can be identified, as the cardiac markers have a highly negative predictive value for mortality in the hospital. A limitation are the cut-off values. The BNP cut-off value for exclusion of an elevated PE risk is below the cut-off value for the exclusion of cardiac failure (100 pg/ml). Even in hemodynamically stable patients with PE showing elevated troponin- or NT-proBNP levels, echocardiographical examination is still necessary to establish a prognosis and to select a therapy. The disadvantage of the diagnostic procedures using natriuretic peptides or troponins alone, however, is the fact that all high risk patients cannot be successfully identified.

Determining the amounts of D-dimer, a natriuretic peptide, in particular NT-proBNP, a cardiac Troponin or any other polypeptide referred to herein according to the present invention relates to measuring the amount or concentration, preferably semi-quantitatively or quantitatively. Measuring can be done directly or indirectly. Direct measuring relates to measuring the amount or concentration of the polypeptide based on a signal which is obtained from the polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the polypeptide. Indirect measuring includes measuring of a signal obtained from a secondary component (i.e. a component not being the polypeptide itself) or a biological read out system, e.g., measurable cellular responses, ligands, labels, or enzymatic reaction products.

In accordance with the present invention, determining the amount of the polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the polypeptide. Moreover, the signal strength can, preferably, be correlated directly or indirectly (e.g. reverse-proportional) to the amount of polypeptide present in a sample. Further suitable methods comprise measuring a physical or chemical property specific for the polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on ELECSYS analyzers, Roche Diagnostics GmbH), CBA (an enzymatic Cobalt Binding Assay, available for example on Roche Hitachi analyzers), and latex agglutination assays (available for example on Roche Hitachi analyzers).

Preferably, determining the amount of a polypeptide comprises the steps of (a) contacting a cell capable of eliciting a cellular response the intensity of which is indicative of the amount of the peptide with the peptide for an adequate period of time, (b) measuring the cellular response.

For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide.

Also preferably, determining the amount of the polypeptide comprises the step of measuring a specific intensity signal obtainable from the polypeptide or a pulmonary surfactant protein in the sample.

As described above, such a signal may be the signal intensity observed at an m/z variable specific for the polypeptide observed in mass spectra or a NMR spectrum specific for the polypeptide.

Further, determining the amount of a polypeptide, preferably, comprises the steps of (a) contacting the peptide with a specific ligand, (b) (optionally) removing non-bound ligand, (c) measuring the amount of bound ligand.

The bound ligand will generate an intensity signal. Binding according to the present invention includes both covalent and non-covalent binding. A ligand according to the present invention can be any compound, e.g., a peptide, polypeptide, nucleic acid, or small molecule, binding to the polypeptide described herein. Preferred ligands include antibodies, nucleic acids, peptides or polypeptides such as receptors for the polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the polypeptide. Specific binding according to the present invention means that the ligand or agent should not bind substantially to ("cross-react" with) another peptide, polypeptide or substance present in the sample to be analyzed. Preferably, the specifically bound polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR, mass spectrometry or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the ligand/polypeptide complex or the ligand which was bound by the polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

Furthermore preferably, determining the amount of a polypeptide comprises (a) contacting a solid support comprising a ligand for the polypeptide as specified above with a sample comprising the polypeptide and (b) measuring the amount of the polypeptide which is bound to the support.

The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

The term "amount" as used herein encompasses the absolute amount of the D-dimer, the natriuretic peptide, in particular NT-proBNP, and the cardiac Troponin, preferably Troponin T or Troponin I, or any other polypeptide referred to herein, the relative amount or concentration of the D-dimer, the natriuretic peptide, in particular NT-proBNP, and the cardiac Troponin, preferably Troponin T or Troponin I, or any other polypeptide referred to herein as well as any value or parameter which correlates thereto. Such values or parameters comprise intensity signal values from all specific physical or chemical properties obtained from the polypeptide referred to herein by direct measurements, e.g., intensity values in mass spectra or NMR spectra. Moreover, encompassed are all values or parameters which are obtained by indirect measurements specified elsewhere in this description, e.g., expression levels determined from biological read out systems in response to the polypeptide or any other polypeptide referred to herein or intensity signals obtained from specifically bound ligands. It is to be understood that values correlating to the aforementioned amounts or parameters can also be obtained by all standard mathematical operations.

D-dimer is a crosslinked fibrin degradation product with an approximate molecular mass of 200 kDa. During blood clotting both coagulation as well as fibrinolysis are activated yielding the active serinproteases thrombin and plasmin. Thrombin splits two fibrinopetide A molecules from fibrinogen. The remaining desAAfibrin monomers form soluble fibrin by polymerisation. The end product is an insoluble fibrin clot formed from the fibrin molecules by crosslinking through the activity of factor XIIIa. Both fibrin and fibrinogen are substrates of plasmin, which hydrolyzes arginine and lysine bonds at multiple sites yielding a variety of cleavage products known as fibrin-fibrinogen degradation products, the smallest of which is D-dimer. D-dimer is derived from crosslinked fibrin and indicates the presence of intravascular activation of coagulation and fibrinolysis. The plasma concentration of fibrin-fibrinogen degradation products, in particular D-dimer, increases during any condition associated with coagulation and fibrinolysis and will therefore be elevated in DVT and PE. An increase in plasma concentrations of fibrin-fibrinogen degradation products, including D-dimer, is also seen in conditions such as malignant disease, pregnancy, postoperative patients, infectious diseases, sepsis, which are all associated with intravascular activation of coagulation. D-dimer is a marker with high sensitivity useful for ruling out deep vein thrombosis and PE with high negative predictive value (for a review see Stein et al. (2004), Annals of Internal Medicine, 140(8), 589-602). The term "D-dimer", preferably, relates to fibrin degradation products that comprise cross-link bonds between two D elements. It is to be understood that said degradation products represent a heterogeneous class of molecules comprising crosslinked D-dimers since said molecules can occur in a wide range of molecular weights and can contain various numbers of the said motif (see e.g. Lippi and Guidi, 2004, Clin Chem 50: 2150-2152). Thus, when the concentration of D-dimer is determined, not only the amount of molecules that consist of two crosslinked D elements are determined but also the amount of larger molecules that contain one or more D-dimer domains. The concentration of D-dimer, preferably, is determined using monoclonal antibodies that are specific for the D-dimer domain. Such antibodies are well known in the art. See, for example, Gaffney P J, Brasher M. Subunit structure of the plasmin-induced degradation products of cross-linked fibrin.

Biochim. Biophys. Acta 1973; 295: 308; Stoetzer K E, Amiral J, Spanuth E. Assays of fibrin degradation products (D-dimer) and their clinical relevance. Haemostasis 1988; 18: 121-122; Knecht M F, Heinrich F, Spanuth E. Evaluation of plasma D-dimer in the course of fibrinotytic therapy of deep vein thrombosis and pulmonary embolism. Thrombosis Research 1992; 67: 213-220; Brill-Edwards P, Lee A. D-dimer testing in the diagnosis of acute venous thromboembolism. Thromb Haemost 1999; 688-94; Kulstad E B, Kulstad C E, Lovell E Q. A rapid turbimetric D-dimer assay has high sensitivity for detection of pulmonary embolism in the ED. Am J Emerg Med 2004; 22: 111-114; Ghanima W, Abdelnoor M, Holmen L O et al. D-dimer level is associated with the extent of pulmonary embolism. Thromb Res 2007; 120: 281-88.

The term fibrin-fibrinogen degradation products (FDP) comprises the products formed during the activation of fibrinolysis by the interaction of plasmin with fibrinogen and the different forms of fibrin. In this process, the inactive precursor protein plasminogen is converted to plasmin, which is the most important fibrinolytic enzyme, but not fibrin-specific. It may also degrade other plasma proteins, including coagulation factors and fibrinogen. The first product formed in the reaction between plasmin and fibrinogen, is designated as fragment X. Fragment X is a clottable derivative (MW=240,000 to 260,000 Da), which is then split asymmetrically into fragment Y (MW=150,000 Da) and a fragment D (MW=100,000 Da). Fragment Y subsequently is split into a second fragment D and a fragment E (MW=50,000 Da). The interaction of plasmin with different forms of fibrin (soluble fibrin, non-crosslinked fibrin, crosslinked fibrin) proceeds via intermediate products, analogous to those described for fibrinogen, since plasmin follows the same interdomainal cleavage pattern in fibrin as in fibrinogen. Non-crosslinked fibrin (desAAfibrin, fibrin I; desAABBfibrin, fibrin II) subsequently yields fragments X, Y, D, E. Crosslinked fibrin I and II consist of very long polymers in which the subunits are covalently linked by isopeptide bonds. Plasmin attacks the fibrin subunits in these polymeric structures in a random order, resulting in smaller soluble fragments of the original polymers with a range of molecular weights. These structures can be degraded to D-dimer fragments, i.e. two covalently bound D-domains, and fragment E.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present invention comprise ANP-type and BNP-type peptides and variants thereof (see e.g. Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro-peptide (134 amino acids in the case of pre-proBNP) comprises a short signal peptide, which is enzymatically cleaved off to release the pro-peptide (108 amino acids in the case of proBNP). The pro-peptide is further cleaved into an N-terminal pro-peptide (NT-pro-peptide, 76 amino acids in case of NT-proBNP) and the active hormone (32 amino acids in the case of BNP, 28 amino acids in the case of ANP). Preferably, natriuretic peptides according to the present invention are NT-proANP, ANP, and, more preferably, NT-proBNP, BNP, and variants thereof. ANP and BNP are the active hormones and have a shorter half-life than their respective inactive counterparts, NT-proANP and NT-proBNP. BNP is rapidly degraded in the blood, whereas NT-proBNP circulates in the blood as an intact molecule and as such, is cleared renally. The in-vivo half-life of NTproBNP is 120 min longer than that of BNP, which is 20 min (Smith 2000, J. Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without loss of recovery. In contrast, storage of BNP for 48 hours at room temperature or at 4° Celsius, leads to a loss of concentration of at least 20% (Mueller loc.cit.; Wu 2004, Clin Chem 50: 867-73.). Therefore, depending on the time-course or properties of interest, either measurement of the active or the inactive forms of the natriuretic peptide can be advantageous. The most preferred natriuretic peptides according to the present invention are NT-proBNP or variants thereof.

The term "NT-proBNP" relates to a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, Bonow 1996, New Insights into the cardiac natriuretic peptides. Circulation 93: 1946-1950. Preferably, human NT-proBNP as used herein is human NT-proBNP as disclosed in EP 0 648 228 B1 or under GeneBank accession number NP-002512.1; GI:4505433. These prior art documents are herewith incorporated by reference with respect to the specific sequences of NT-proBNP and variants thereof disclosed therein.

The NT-proBNP, referred to in accordance with the present invention, further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are the essential immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the specific human NT-proBNP sequences referred to above. Biological and/or immunological NT-proBNP properties can be detected by the assay described in Karl et al. (Karl 1999. Development of a novel, N-Terminal-proBNP (NT-proBNP) assay with a low detection limit. Scand J Clin Invest 59:177-181), Yeo et al. (Yeo 2003. Multicenter evaluation of the Roche NT-proBNP assay and comparison to the Biosite Triage assay. Clinica Chimica Acta 338:107-115). Variants also include posttranslationally modified NT-proBNPs such as glycosylated, myristylated or phosphorylated variants.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac troponin refers to troponin T and/or troponin I, and, most preferably, to troponin T. It is to be understood that isoforms of troponins may be determined in the method of the present invention together, i.e. simultaneously or sequentially, or individually, i.e. without determining the other isoform at all. Amino acid sequences for human troponin T and human troponin I are disclosed in Anderson, loc cit and Ferrieres 1998, Clinical Chemistry, 44: 487-493.

The term "cardiac troponin" encompasses also variants of the aforementioned specific troponins, i.e., preferably, of troponin I, and more preferably, of troponin T. Such variants have at least the same essential biological and immunological properties as the specific cardiac troponins In particular, they share the same essential biological and immunological properties if they are detectable by the same specific assays referred to in this specification, e.g., by ELISAs using polyclonal or monoclonal antibodies specifically recognizing the said cardiac troponins Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins Further included are variants which differ due to posttranslational modifications such as phosphorylation or myristylation.

A particularly preferred troponin T assay in the context of the present invention is the ELECSYS 2010 analyzer (Roche Diagnostics) with a detection limit of from 0.001 ng/ml to 0.0015 ng/ml.

A variant in accordance with the present invention is also a peptide or polypeptide which has been modified after collection of the sample, for example by covalent or non-covalent attachment of a label, particularly a radioactive or fluorescent label, to the peptide.

The term "sample" refers to a sample of a body fluid, to a sample of separated cells or to a sample from a tissue or an organ. Samples of body fluids can be obtained by well known techniques and include, preferably, samples of blood, plasma, serum or urine. Tissue or organ samples may be obtained from any tissue or organ by, e.g., biopsy. Separated cells may be obtained from the body fluids or the tissues or organs by separating techniques such as centrifugation or cell sorting.

Comparing as used herein encompasses comparing the amount of the D-dimer, the natriuretic peptide, in particular NT-proBNP, and the cardiac Troponin, preferably Troponin T or Troponin I, or any other polypeptide referred to herein comprised by the sample to be analyzed with an amount of a suitable reference source specified below in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (d) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically providing a differential diagnosis for the diseases referred to herein in a suitable output format.

The term "reference amount" as used herein refers to an amount which allows assessing whether a subject suffers from PE, by a comparison as referred to above. Accordingly, the reference may either be derived from a subject known to suffer from PE. It is to be understood that if a reference from a subject is used which suffers from PE, an amount NT-proBNP in a sample of a test subject being essentially identical to said reference amount shall be indicative for s PE. Likewise, if a reference from a subject known not to suffer from PE is used, an amount of NT-proBNP in a sample of a test subject being essentially identical to said reference amount shall be indicative for the non-occurrence of a PE. The reference amount applicable for an individual subject may vary depending on various physiological parameters such as age, gender, or subpopulation. Thus, a suitable reference amount may be determined by the method of the present invention from a reference sample to be analyzed together, i.e. simultaneously or subsequently, with the test sample.

The levels of fibrin-fibrinogen degradation products can be measured using a variety of immunoassay techniques. Commonly used methods for measuring fibrin-fibrinogen degradation products are techniques using latex particles coated monoclonal antibodies against neoantigenic determinants on plasmin-derived fibrin-fibrinogen fragments X, Y, D and E.

The prevalence of PE in patients in whom the disease is suspected is low. Pulmonary angiography is the definite criterion standard for the diagnosis of PE but this method is invasive, costly and often difficult to interpret. D-dimer, when assayed by a quantitative ELISA or ELISA-derived method has been found to be highly sensitive (>99%) in acute PE at a cutoff value of 500 µg/L. Hence, a D-dimer level below this value rules out PE. On the other hand, the specificity of D-dimer is poor. Because D-dimer is produced in the presence of intravascular activation of coagulation and fibrinolysis in a wide variety of clinical conditions, such as cancer, inflammation, infection, sepsis, necrosis, a D-dimer level above 500 µg/L has a poor positive predictive value for PE, and cannot rule in the disease. Therefore, the diagnostic algorithm to rule in PE comprises pulmonary angiography, spiral computed tomography, lower limb venous compression ultrasonography, and lung perfusion and ventilation scintigraphy. For risk stratification of PE, echocardiography allows to assess right ventricular overload and dysfunction. Echocardiographic findings of haemodynamically significant PE include a dilated, hypokinetic right ventricle, dilated proximal pulmonary arteries, disturbed flow velocity, and other haemodynamic abnormalities. On the other hand, haemodynamically important PE is unlikely in a patient with a normal echocardiogram (Wolfe M W, Feldstein M I, Parker J A et al.: Prognostic significance of right ventricular hypokinesis and perfusion lung scan defects in PE).

However, echocardiography has some technical limitations and may not always be readily available. It cannot be used for quantitative assessment of the severity of right ventricular damage and dysfunction. Moreover, echocardiography is time consuming and difficult to interprete. Therefore non-invasive and rapid diagnostic approaches are needed for the diagnosis and risk stratification of PE.

The method according to the invention comprises the determination of at least three markers, whereby at least one marker of intravascular activation of coagulation and fibrinolysis, at least one marker of cardiac ischemia and necrosis, and at least one marker of ventricular dysfunction is determined. The marker of intravascular activation of coagulation and fibrinolysis can be selected, for example, from fibrin-fibrinogen degradation products, in particular D-dimer. Troponin T or troponin I can be determined as ischemic and necrosis markers. The marker of ventricular dysfunction can be selected from neurohormonal markers like natrial natriuretic peptide (ANP), brain natriuretic peptide (BNP), or N-terminal fragments of the respective propeptides NT-proANP and NT-proBNP.

The amounts/levels of the markers of the present invention (a fibrin-fibrinogen degradation products, in particular D-dimer, a natriuretic peptide, in particular NT-proBNP, and a cardiac troponin, in particular troponin T or troponin I) indicating if an individual suffers from a pathophysiological state or is an healthy individual, are determined by methods known to the person skilled in the art.

In general, for determining such an amount/level indicating if an individual suffers from a pathophysiological state or is a healthy individual ("threshold", "reference amount"), the amount(s)/level(s) of the respective peptide or peptides are determined in appropriate patient groups comprising healthy individuals and individuals suffering from the pathopysiological state which is to be determined by the respective marker(s) using validated analytical methods. The results are collected and analyzed by statistical methods known to the person skilled in the art. The obtained threshold values are then established in accordance with the desired probability of suffering from the disease which is linked to the particular threshold value. For example, it may be useful to choose the median value, the 60th, 70th, 80th, 90th, 95th or even the 99th percentile of the healthy and/or non-healthy patient collective, in order to establish the threshold value(s).

The diagnosis if individuals are healthy or suffer from a certain pathophysiological state is made by established methods known to the person skilled in the art. The methods differ in respect to the individual pathophysiological state.

For example (as already mentioned beforehand) diagnostic algorithm to rule in PE comprises pulmonary angiography, spiral computed tomography, lower limb venous compression ultrasonography, lung perfusion and ventilation scintigraphy, and also echocardiography to assess right ventricular overload and dysfunction and haemodynamic abnormalities. Echocardiography is used to assess various cardiac dysfunctions, like heart failure, myocardial infarction and/or cardiomyopathy.

Accordingly, the present invention also comprises a method of determining the threshold level indicating if an individual suffers from PE and/or indicating the severity (class) of the disease, comprising the steps of determining in appropriate patient groups the levels of the appropriate marker(s), in general a fibrin-fibrinogen degradation products, in particular D-dimer, a natriuretic peptide, in particular NT-proBNP, and a cardiac troponin, in particular troponin T or troponin I, collecting the data and analyzing the data by statistical methods and establishing the threshold values.

It has been found that an amount of a fibrin-fibrinogen degradation product, in particular D-dimer larger than the threshold in combination with an amount of a cardiac troponin, preferably troponin T or troponin I, and in combination with and amount of a natriuretic peptide, preferably NT-proBNP larger than the threshold (i.e. a reference amount) are indicative for the severity of PE. The preferred threshold for D-dimer is 0.5 mg/L. The preferred threshold for cardiac troponin, in particular cardiac troponin T, is 0.03 ng/mL. The preferred threshold for the natriuretic peptide, in particular NT-proBNP, is 500 pg/mL. Accordingly, a subject having an amount of the mentioned peptides equal to or larger than the cited amounts suffers from PE. It is to be understood that the aforementioned amounts may vary due to statistics and errors of measurement.

In one embodiment of the present invention, the amount of D-dimer is determined and, according to the result of this step, it may reveal not necessary to measure the amounts of the natriuretic peptide and the cardiac troponin. This may be the case when a low amount of D-dimer, excluding that the subject is suffering from PE, is measured. Respective amounts excluding PE are those below the threshold values cited beforehand, i.e. below 500 µg/L, preferably 10%, more preferably 20%, even more preferably 30%, in particular 50% lower than 500 µg/L.

Thanks to the present invention, it is possible to establish a reliable and easy diagnosis of an individual suffering from PE and to assess the risk of patients with confirmed PE without using technical or invasive diagnostic tests like angiography, echocardiography etc.

In a further, preferred embodiment of the present invention, it is also possible to establish the severity of the PE. According to the severity of the disease, PE is classified in the following risk groups/severity classes:

Risk group I: symptomatic non-massive PE, haemodynamic stable without right ventricular dysfunction (systolic arterial pressure>100 mmHg)

Risk group II: submassive PE, haemodynamic stable with right ventricular dysfunction Risk group III: massive PE, shock and hypotension (systolic arterial pressure<100 mmHg), heart rate>100/min Risk group IV: resuscitation necessary (see literature: Interdisziplinäre S2-Leitlinie: Diagnostik und Therapie der Bein- und Beckenvenen-Thrombose und der Lungenembolie. Phlebologie 2005; 34: 47-64).

In the present application, the terms "risk group" and "severity class" will be used interchangeably, wherein the terms refer to the severity of PE and the risk connected therewith.

The following reference amounts of D-dimer, Troponin T and NT-proBNP have been found to be characteristic for the respective risk groups. The patient with confirmed PE is to be assigned to the respective group according to the following algorithm:

1. If three parameters meet the criteria of one group, the patient is to assigned to this group.
   (Example: D-dimer: 800 µg/L; Troponin T: 0.01 ng/ml; NT-proBNP: 300 pg/ml)
2. If two of three parameters meet the criteria of one group, the patient is to be assigned to this group.
   (Example 1: D-dimer: 2500 µg/L; Troponin T: 0.08 ng/ml; NT-proBNP: 3000 pg/ml to be assigned to risk group II)
   (Example 2: D-dimer: 2500 µg/L; Troponin T: 0.4 ng/ml; NT-proBNP: 3000 pg/ml to be assigned to risk group III)
3. If all three parameters meet the criteria of three different groups, the patient is to be assigned to the group with the parameter with the highest value
   (Example 1: D-dimer: 700 µg/L; Troponin T: 0.2 ng/ml; NT-proBNP: 6000 pg/ml; to be assigned to risk group IV)
   (Example 2: D-dimer: 17000 µg/L; Troponin T: 0.02 ng/ml; NT-proBNP: 3000 pg/ml; to be assigned to risk group IV)

Risk group I:
D-dimer: 500 to <2000 µg/L
Troponin T; <0.03 ng/ml
NT-proBNP: <500 pg/ml Risk group II:
D-dimer: 2000 to <6000 µg/L
Troponin T; 0.03 ng/ml
NT-proBNP: 500 pg/ml Risk group III:
D-dimer: 6000-12000 µg/L
Troponin T; >0.1 ng/ml
NT-proBNP: 500 pg/ml
Risk group IV:
D-dimer: >12000 µg/L
Troponin T; >0.1 ng/ml
NT-proBNP: >5000 pg/ml Accordingly, in this variant of the present invention, the method of the invention is a method of classifying the individual in different risk groups/different severity classes, comprising steps a), b), c) and d) as in the method of diagnosing PE, and wherein step d) includes the step of classifying the individual (instead of establishing the diagnosis). This method can also be referred to as diagnosing the severity of PE.

Thus, the present invention comprises a method of classifying an individual suffering from PE in different risk groups, wherein the individual preferably shows a level (amount) of D-dimer of >500 µg/L, and wherein the method comprises the following steps:
bi) determining the amount of a natriuretic peptide in a sample of the subject;
ci) determining the amount of a cardiac troponin in a sample of the subject;
di) comparing the amounts determined in steps bi) to di) to reference amounts and classifying the individual.

It is to be understood that the aforementioned amounts may vary due to statistics and errors of measurement as well as the time passed since onset of symptoms (biological time course of concentrations determined by clearing mechanisms).

Advantageously, it has been found that the amounts of the mentioned peptides present in a sample of a subject allow for a differential diagnosis with respect to the cause of the said symptoms, i.e. it can be diagnosed whether the PE severity belongs to class I, II, III or IV. Thanks to the present invention, subjects and, in particular, emergency patients can be more readily and reliably diagnosed and subsequently treated according to the result of the said differential diagnosis.

The explanations and definitions of the terms made above and herein below apply accordingly for all embodiments characterized in this specification and the claims.

The amounts of the polypeptides which are within the present invention can be determined simultaneously or subsequently, preferably simultaneously.

Under "simultaneously" as used herein is to be understood that the amounts of all markers are to be determined at essentially the same time or exactly the same time. All markers may be determined for the same sample. Alternatively, they may be determined in a different sample. However, the said different samples shall be obtained from the same subject at the same time.

In a further embodiment, the present invention also encompasses a method of deciding on the therapy of a subject suffering from PE, comprising the steps of:
a) determining the amount of fibrin-fibrinogen degradation products, in particular D-dimer, in a sample of the subject;
b) determining the amount of a natriuretic peptide in a sample of the subject;
c) determining the amount of a cardiac troponin in a sample of the subject;
d) comparing the amounts determined in steps a) to c) to reference amounts, thereby establishing the said decision.

The decision taken in step d) is preferably established after classifying the individual in different severity classes according to the values of the measured peptides.

The therapy according to the present invention includes, preferably, the following therapeutic measures, in accordance with the severity of the PE:
Risk group I: anticoagulation with heparins, thrombolysis, in particular with urokinase, streptokinase and recombinant tissue plasminogen activator (rTPA)
Risk group II: if no contraindication exists, anticoagulation with heparins, thrombolysis, in particular with urokinase, streptokinase and recombinant tissue plasminogen activator (rTPA)
Risk group III: anticoagulation with heparins, thrombolysis, in particular with urokinase, streptokinase and recombinant tissue plasminogen activator (rTPA)
Risk group IV: anticoagulation with heparins, thrombolysis, in particular with urokinase, streptokinase and recombinant tissue plasminogen activator (rTPA), or embolectomy Accordingly, "fibrinolytics" are preferably used which comprise urokinase, streptokinase, and recombinant tissue plasminogen activator (rTPA) and variants thereof having the same physiological function. Heparin according to the present invention comprises unfractionated heparin (UFH), low molecular weight heparin (LMWH), heparinoides and variants thereof.

In one embodiment of this variant of the present invention, the amount of D-dimer is determined and, according to the result of this step, it may reveal not necessary to measure the amounts of the natriuretic peptide and the cardiac troponin. This may be the case when an amount of D-dimer below the cutoff value of 500 µg/L is measured, excluding that the subject is suffering from PE with the subject thus not being in need of a cardiac therapy. Respective amounts excluding PE are those below the threshold values cited beforehand, i.e. below 500 µg/L In a further embodiment, the present invention also encompasses a method of monitoring the therapy of a subject suffering from PE, which comprises the steps of the method of deciding on the therapy, as cited beforehand, and the additional step
e) again determining the amounts of the peptides determined in the preceding method of deciding.

This method may include an adaptation of the therapy, in accordance with the values determined. For example, a subject having a PE severity according to one of the classes I to IV may be reclassified into a different class, including an adaptation of the respective treatment, as laid out beforehand.

The present invention also pertains to a device adapted for carrying out the method of the present invention comprising:
a) means for determining the amount of D-dimer;
b) means for determining the amount of a natriuretic peptide, in particular NT-proBNP; and
c) means for determining the amount of a cardiac troponin.

The term "device" as used herein relates to a system of means comprising at least the aforementioned means operatively linked to each other as to allow the prediction. Preferred means for determining the amount of the said polypeptides and means for carrying out the comparison with reference amounts are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to diagnose or distinguish between the diseases referred to herein. Preferably, the means are comprised by a single device in such a case. Said device may accordingly include an analyzing unit for the measurement of the amount of the peptides in a sample and a computer unit for processing the resulting data for the differential diagnosis. Alternatively, where means such as test stripes are used for determining the amount of the peptides, the means for diagnosing may comprise control stripes or tables allocating the determined amount to an amount known to be accompanied with (i) an acute or a chronic lung embolism and (ii) a singular or a multiple lung embolism. The test stripes are, preferably, coupled to a ligand which specifically binds to the natriuretic peptide or pulmonary surfactant protein. The strip or device, preferably, comprises means for detection of the binding of said peptides to the said ligand. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of parametric diagnostic raw data, preferably, as absolute or relative amounts. It is to be understood that these data will need interpretation by the clinician. However, also envisage are expert system devices wherein the output comprises processed diagnostic raw data the interpretation of which does not require a specialized clinician. Further preferred devices comprise the analyzing units/devices (e.g., biosensors, arrays, solid supports coupled to ligands specifically recognizing the polypeptides, Plasmon surface resonance devices, NMR spectrometers, mass-spectrometers etc.) or evaluation units/devices referred to above in accordance with the method of the invention.

Under "adopted for carrying out" it shall be understood that the device is capable of automatically carrying out the methods referred to above. For such an adaptation, it is envisaged that the device comprises implemented rules for making a comparison between the determined amounts of the polypeptides and a reference amount which may be also determined by the device from a reference sample or which may virtually exist as a stored value. Moreover, the device may comprise implemented rules for determining a significant decrease in the amounts of the polypeptides between two at least different samples (i.e. the sample of a first and a second time point). The implementation of such rules in the device is, preferably, accomplished by an algorithm provided in the form a storable program code run on a computer or data processing unit.

Finally, the present invention relates to a kit for carrying out the method of the present invention comprising:
a) means for determining the amount of fibrin-fibrinogen degradation products, in particular D-dimer;
b) means for determining the amount of a natriuretic peptide, in particular NT-proBNP; and
c) means for determining the amount of a cardiac troponin.
d) instructions for carrying out the aforementioned methods.

The term "kit" as used herein refers to a collection of the aforementioned means, preferably, provided in separately or within a single container. The container, also preferably, comprises instructions for carrying out the method of the present invention. The invention, thus, relates to a kit comprising a means or an agent for measuring the respective polypeptides. Such means or agent may be any suitable means or agent known to the person skilled in the art. Examples for such means or agents as well as methods for their use have been given in this specification. For example, a suitable agent may be any kind of ligand or antibody capable of specifically binding to a polypeptide referred to herein above. The kit may also comprise any other components deemed appropriate in the context of determining the amount(s) of the respective biomarkers, such as suitable buffers, filters, etc. Preferably, the kit may additionally comprise instructions, e.g., a user's manual for interpreting the results of any determination(s) with respect to the diagnoses provided by the methods of the present invention. Particularly, such manual may include information for allocating the amounts of the determined polypeptides to the kind of diagnosis, i.e. to a singular or multiple lung embolism or to an acute or chronic lung embolism. Details are to be found elsewhere in this specification. Additionally, such user's manual may provide instructions about correctly using the components of the kit for determining the amount(s) of the respective biomarker. A user's manual may be provided in paper or electronic form, e.g., stored on CD or CD ROM. The present invention also relates to the use of said kit in any of the methods according to the present invention.

All references cited in this specification are herewith incorporated by reference with respect to their entire disclosure content and the disclosure content specifically mentioned in this specification.

The following Examples merely illustrate the invention. It shall, whatsoever, not be construed as to limit the scope of the invention. In the present study, the amounts of the respective polypeptides are measured in blood samples. For determination of NT-proBNP and troponin T, the ELECSYS test (Roche Diagnostics, Germany) was used. D-dimer levels were determined in citrated plasma samples using the STA LIATEST D-Di (STAGO, France), and Tina-quant (a) D-Dimer (Roche Diagnostics, Germany).

EXAMPLE 1

Multimarker Approach in Patients with Confirmed PE

A total of 12 patients with suspected PE are included in the study.

The patients showed elevated D-dimer concentrations above the cutoff value 500 µg/L. The diagnosis PE was confirmed by pulmonary angiography. D-dimer, the natriuretic peptides NT-proANP and NT-proBNP as well as troponin T and high sensitivity troponin T were determined for risk stratification. The results are displayed in table 1. The patients were classified into the risk groups I-IV according to the concentrations of D-dimer, troponin T, and NT-proBNP, if two of three values met the following criteria:

Patients in risk group I:
D-dimer: 500-<2000 µg/L
Troponin T: <0.03 ng/ml
NT-proBNP: <500 pg/ml
Patients in risk group II:
D-dimer: 2000-<6000 µg/L
Troponin T: 0.03 ng/ml
NT-proBNP: 500 pg/ml
Patients in risk group III:
D-dimer: 6000-12000 µg/L
Troponin T: >0.1 ng/ml
NT-proBNP: 500 pg/ml
Patients in risk group IV:
D-dimer: >12000 µg/L
Troponin T: >1.0 ng/ml
NT-proBNP: >5000 pg/ml

TABLE 1

D-dimer, NT-proBNP and Troponin T in risk stratification and therapy decision of patients with confirmed PE

| Submission | Pt No | Blood sampling | NT-proBNP pg/ml | NT-proANP pg/ml | hs TnT pg/ml | TnT ng/ml | D-dimer μg/L | Risk Group | Therapy |
|---|---|---|---|---|---|---|---|---|---|
| 03.01.2006 | 40 | 03.01.2006 | 1998 | 635 | 152.15 | 0.151 | 800 | III | urokinase |
| 10.06.2006 | 70 | 10.06.2006 | 5304 | 3441 | 85.86 | 0.076 | 1109 | IV | actilyse |
| 27.05.2006 | 63 | 27.05.2006 | 37 | 635 | | 0.001 | 1270 | I | heparin |
| 07.01.2006 | 27 | 07.01.2006 | 89 | 635 | 0.62 | 0.001 | 1243 | I | heparin |
| 09.01.2006 | 31 | 09.01.2006 | 5 | 635 | | 0.001 | 1713 | I | heparin |
| 01.08.2005 | 53 | 01.08.2005 | 63 | 635 | 146.74 | 0.133 | 1766 | II | heparin |
| 15.01.2006 | 21 | 15.01.2006 | 8129 | 635 | 45.32 | 0.026 | 2190 | IV | actilyse |
| 12.02.2006 | 16 | 12.02.2006 | 3599 | 7556 | 235.07 | 0.235 | 2299 | III | urokinase |
| 29.05.2006 | 56 | 29.05.2006 | 21316 | 9538 | 61.59 | 0.054 | 3000 | III | urokinase |
| 10.01.2006 | 25 | 10.01.2006 | 292 | 635 | 5.7 | 0.001 | 2332 | I | heparin |
| 06.02.2006 | 11 | 07.02.2006 | 3250 | 7874 | 77.41 | 0.072 | 3310 | II | heparin |
| 27.02.2006 | 1 | 27.02.2006 | 1500 | 1702 | 182.96 | 0.177 | 7370 | III | urokinase |

EXAMPLE 2

Therapy Decision in Patients Suffering from Different Degrees of PE

The patients diagnosed as described above are treated as follows:
Group I: anticoagulation therapy with heparins
Group II: anticoagulation therapy with heparins or thrombolysis if no contraindication exists
Group III: thrombolysis (urokinase or streptokinase)
Group IV: thrombolysis (actilyse) or embolectomy

EXAMPLE 3

A 52-year old man was admitted with clinical signs of PE suffering dyspnoea for 10 days. He has a history of postoperative DVT 5 years ago but no evidence of thrombophilia. The diagnosis of PE was confirmed by pulmonary angiography. The following marker levels were measured:
D-dimer: 2130 μg/L
Troponin T: 0.08 ng/ml
NT-proBNP: 465 pg/ml

| Classification | | Results |
|---|---|---|
| Risk group I | | |
| D-dimer | 500-<2000 μg/L | |
| Troponin T | <0.03 ng/ml | |
| NT-proBNP | <500 pg/ml | NT-proBNP: 465 pg/ml |
| Risk group II | | |
| D-dimer | 2000-<6000 μg/L | D-dimer: 2130 μg/L |
| Troponin T | ≧0.03 ng/ml | Troponin T: 0.08 ng/ml |
| NT-proBNP | ≧500 pg/ml | |
| Risk group III | | |
| D-dimer | 6000-12000 μg/L | |
| Troponin T | >0.1 ng/ml | |
| NT-proBNP | ≧500 pg/ml | |
| Risk group IV | | |
| D-dimer | >12000 μg/L | |
| Troponin T | >1.0 ng/ml | |
| NT-proBNP | >5000 pg/ml | |

The patient was assigned to risk group II and treated with heparin without bleeding complications. After 8 days he was discharged.

EXAMPLE 4

A 75-year old female was admitted with chest pain and dyspnoea at rest to the emergency department. She had no history of pulmonary diseases or PE. ECG showed no signs of acute coronary syndrome. The diagnosis of PE was confirmed by pulmonary angiography and spiral CT which were performed immediately after admission. The following marker levels were measured:
D-dimer: 3200 μg/L
Troponin T: 0.04 ng/ml
NT-proBNP: 11550 pg/ml

| Classification | | Results |
|---|---|---|
| Risk group I | | |
| D-dimer | 500-<2000 μg/L | |
| Troponin T | <0.03 ng/ml | |
| NT-proBNP | <500 pg/ml | |
| Risk group II | | |
| D-dimer | 2000-<6000 μg/L | D-dimer: 3200 μg/L |
| Troponin T | >0.03 ng/ml | Troponin T: 0.04 ng/ml |
| NT-proBNP | ≧500 pg/ml | |
| Risk group III | | |
| D-dimer | 6000-12000 μg/L | |
| Troponin T | >0.1 ng/ml | |
| NT-proBNP | ≧500 pg/ml | |
| Risk group IV | | |
| D-dimer | 12000 μg/L | |
| Troponin T | >1.0 ng/ml | |
| NT-proBNP | >5000 pg/ml | NT-proBNP: 11550 pg/ml |

The patient was assigned to risk group II and treated with heparin.

EXAMPLE 5

A 37-year old man was admitted with clinical signs suspicious of PE suffering dyspnoea 10 days after arthroscopy. The diagnosis of PE was confirmed by pulmonary angiography. The following marker levels were measured:

D-dimer: 2130 µg/L

Troponin T: 0.23 ng/ml

NT-proBNP: 465 pg/ml

| Classification | | |
|---|---|---|
| | | Results |
| Risk group I | | |
| D-dimer | 500-<2000 µg/L | |
| Troponin T | <0.03 ng/ml | |
| NT-proBNP | <500 pg/ml | NT-proBNP: 465 pg/ml |
| Risk group II | | |
| D-dimer | 2000-<6000 µg/L | D-dimer: 2130 µg/L |
| Troponin T | ≧0.03 ng/ml | |
| NT-proBNP | ≧500 pg/ml | |
| Risk group III | | |
| D-dimer | 6000-12000 µg/L | |
| Troponin T | >0.1 ng/ml | Troponin T: 0.23 ng/ml |
| NT-proBNP | ≧500 pg/ml | |
| Risk group IV | | |
| D-dimer | >12000 µg/L | |
| Troponin T | >1.0 ng/ml | |
| NT-proBNP | >5000 pg/ml | |

The patient was assigned to risk group II and admitted to the intensive care unit and treated with heparin without bleeding complications. After 4 days he was discharged from the intensive care unit.

EXAMPLE 6

A 80-year old man developed clinical signs suspicious of PE after prostate surgery. The diagnosis of PE was confirmed by pulmonary angiography. The following marker levels were measured:

D-dimer: 2130 µg/L

Troponin T: 0.018 ng/ml

NT-proBNP: 3719 pg/ml

| Classification | | |
|---|---|---|
| | | Results |
| Risk group I | | |
| D-dimer | 500-<2000 µg/L | D-dimer: 1100 µg/L |
| Troponin T | <0.03 ng/ml | Troponin T: 0.018 ng/ml |
| NT-proBNP | <500 pg/ml | |
| Risk group II | | |
| D-dimer | 2000-<6000 µg/L | |
| Troponin T | ≧0.03 ng/ml | |
| NT-proBNP | ≧500 pg/ml | |
| Risk group III | | |
| D-dimer | 6000-12000 µg/L | |
| Troponin T | >0.1 ng/ml | |
| NT-proBNP | ≧500 pg/ml | NT-proBNP: 3719 pg/ml |
| Risk group IV | | |
| D-dimer | >12000 µg/L | |
| Troponin T | >1.0 ng/ml | |
| NT-proBNP | >5000 pg/ml | |

The patient was assigned to risk group I and admitted to the intensive care unit and treated with heparin without bleeding complications. After 2 days he was discharged from the intensive care unit.

EXAMPLE 7

A 55-year old woman was admitted to the emergency unit. She had collapsed and was in critical condition (systolic blood pressure 85 mmHg, heart rate 142 bpm). The diagnosis of PE was confirmed by pulmonary angiography. The following marker levels were measured:

D-dimer: 8109 µg/L

Troponin T: 1.86 ng/ml

NT-proBNP: 11779 pg/ml

| Classification | | |
|---|---|---|
| | | Results |
| Risk group I | | |
| D-dimer | 500-<2000 µg/L | |
| Troponin T | <0.03 ng/ml | |
| NT-proBNP | <500 pg/ml | |
| Risk group II | | |
| D-dimer | 2000-<6000 µg/L | |
| Troponin T | ≧0.03 ng/ml | |
| NT-proBNP | ≧500 pg/ml | |
| Risk group III | | |
| D-dimer | 6000-12000 µg/L | D-dimer: 8109 µg/L |
| Troponin T | >0.1 ng/ml | |
| NT-proBNP | ≧500 pg/ml | |
| Risk group IV | | |
| D-dimer | >12000 µg/L | |
| Troponin T | >1.0 ng/ml | Troponin T: 1.86 ng/ml |
| NT-proBNP | >5000 pg/ml | NT-proBNP: 11779 pg/ml |

The patient was assigned to risk group IV and admitted to the intensive care unit. Despite thrombolysis using urokinase she died the day after admission.

What is claimed is:

1. A device for classifying a subject suffering from pulmonary embolism into one of a pulmonary embolism severity risk group: Risk Group I, symptomatic non-massive PE, haemodynamic stable without right ventricular dysfunction (systolic arterial pressure >100 mmHg); Risk Group II, submassive PE, haemodynamic stable with right ventricular dysfunction; Risk Group III, massive PE, shock and hypotension (systolic arterial pressure <100 mmHg), heart rate >100/min; and Risk Group IV, resuscitation necessary, the device comprising:

means for determining an amount of D-dimer in a sample from the subject, means for determining an amount of NT-proBNP in a sample from the subject, means for determining an amount of troponin T in a sample from the subject, implemented rules for comparing the determined amounts of D-dimer, NT-proBNP, and troponin T to reference amounts for D-dimer, NT-proBNP, and troponin T, respectively, the reference amounts existing as stored values, and implemented rules for classifying the subject into one of said pulmonary embolism severity risk groups on the basis of the comparisons, and means for implementing the rules, wherein said stored reference amounts include reference amounts of D-dimer from 500 to less than 2000 µg/L, troponin T less than 0.03 ng/ml, and NT-proBNP less than 500 pg/ml that are indicative for Risk Group I; reference amounts of D-dimer from 2000 to less than 6000 µg/L, troponin T less than 0.03 ng/ml, and NT-proBNP less than 500 pg/ml that are indicative for Risk Group II; reference amounts of D-dimer from 6000 to 12000 µg/L, troponin T greater than 0.1 ng/ml, and NT-proBNP equal to or greater than 500 pg/ml that are indicative for Risk Group III; and reference amounts of D-dimer greater than 12000 µg/L, troponin T greater than 1.0 ng/ml, and NT-proBNP greater than 5000 pg/ml that are indicative for Risk Group IV.

2. The device of claim 1, wherein said means for determining the amount of D-dimmer comprises at least one of a mass spectrometer, an NMR analyzer and a chromatography device.

3. The device of claim 1, wherein said means for determining the amount of NT-proBNP comprises at least one of a mass spectrometer, an NMR analyzer and a chromatography device.

4. The device of claim 1, wherein said means for determining the amount of troponin T comprises at least one of a mass spectrometer, an NMR analyzer and a chromatography device.

5. The device of claim 1, wherein said means for determining the amount of D-dimer, said means for determining the amount of NT-proBNP, and said means for determining the amount of troponin T comprise an automated analyzer.

6. The device of claim 1, wherein the sample is one of blood, plasma, serum and urine.

7. The device of claim 1, wherein the means for implementing the rules comprises a computing device having a database.

8. A kit for classifying a subject suffering from pulmonary embolism into one of a pulmonary embolism severity risk group: Risk Group I, symptomatic non-massive PE, haemodynamic stable without right ventricular dysfunction (systolic arterial pressure >100 mmHg); Risk Group II, submassive PE, haemodynamic stable with right ventricular dysfunction; Risk Group III, massive PE, shock and hypotension (systolic arterial pressure <100 mmHg), heart rate >100/min; and Risk Group IV, resuscitation necessary, the kit comprising:

means for determining an amount of D-dimer in a sample from the subject,
means for determining an amount of NT-proBNP in a sample from the subject,
means for determining an amount of troponin T in a sample from the subject,
instructions for carrying out the determinations and for making comparisons of the determined amounts of D-dimer, NT-proBNP, and troponin T to reference amounts for D-dimer, NT-proBNP, and troponin T, respectively, wherein the reference amounts exist as stored values, and instructions for classification of the subject into one of said pulmonary embolism risk groups based on the comparisons, and
means for implementing the instructions, wherein said stored reference amounts include reference amounts of D-dimer from 500 to less than 2000 µg/L, troponin T less than 0.03 ng/ml, and NT-proBNP less than 500 pg/ml that are indicative for Risk Group I; reference amounts of D-dimer from 2000 to less than 6000 µg/L, troponin T less than 0.03 ng/ml, and NT-proBNP less than 500 pg/ml that are indicative for Risk Group II; reference amounts of D-dimer from 6000 to 12000 µg/L, troponin T greater than 0.1 ng/ml, and NT-proBNP equal to or greater than 500 pg/ml that are indicative for Risk Group III; and reference amounts of D-dimer greater than 12000 µg/L, troponin T greater than 1.0 ng/ml, and NT-proBNP greater than 5000 pg/ml that are indicative for Risk Group IV.

9. The kit of claim 8, wherein said means for determining the amount of D-dimer comprises a ligand having specific binding affinity for D-dimer polypeptide.

10. The kit of claim 9, wherein the ligand is one of an antibody, a nucleic acid, and a polypeptide receptor.

11. The kit of claim 9, wherein said means further comprises a second ligand having specific binding affinity for the ligand having specific binding affinity for D-dimer polypeptide.

12. The kit of claim 11, wherein the second ligand includes a tag consisting of one of an enzymatically active label, a fluorescent label, a radioactive label, a biotin label, and a strepavidin label.

13. The kit of claim 8, wherein said means for determining the amount of NT-proBNP comprises a ligand having specific binding affinity for NT-proBNP polypeptide.

14. The kit of claim 13, wherein the ligand is one of an antibody, a nucleic acid, and a polypeptide receptor.

15. The kit of claim 13, wherein said means further comprises a second ligand having specific binding affinity for the ligand having specific binding affinity for NT-proBNP polypeptide.

16. The kit of claim 15, wherein the second ligand includes a tag consisting of one of an enzymatically active label, a fluorescent label, a radioactive label, a biotin label, and a strepavidin label.

17. The kit of claim 8, wherein said means for determining the amount of troponin T comprises a ligand having specific binding affinity for troponin T polypeptide.

18. The kit of claim 17, wherein the ligand is one of an antibody, a nucleic acid, and a polypeptide receptor.

19. The kit of claim 17, wherein said means further comprises a second ligand having specific binding affinity for the ligand having specific binding affinity for troponin T polypeptide.

20. The kit of claim 19, wherein the second ligand includes a tag consisting of one of an enzymatically active label, a fluorescent label, a radioactive label, a biotin label, and a strepavidin label.

* * * * *